United States Patent [19]
Ito et al.

[11] Patent Number: 5,590,053
[45] Date of Patent: Dec. 31, 1996

[54] METHOD OF DETERMINING A SPACE GROUP

[75] Inventors: Tatsuya Ito; Masahito Kawai; Yoshihito Yasukawa, all of Kawasaki, Japan

[73] Assignee: Fujitsu Limited, Japan

[21] Appl. No.: 278,155

[22] Filed: Jul. 21, 1994

[30] Foreign Application Priority Data

Oct. 29, 1993 [JP] Japan .................................. 5-271501

[51] Int. Cl.$^6$ ................................................ G06F 17/10
[52] U.S. Cl. ............................ 364/499; 364/578; 364/496; 364/497; 364/498; 423/308
[58] Field of Search ................................. 423/308, 309, 423/311; 364/496, 497, 498, 499, 578, 554

[56] References Cited

FOREIGN PATENT DOCUMENTS 2254458  10/1992  United Kingdom .

OTHER PUBLICATIONS

Matsuura, Y.; "AUTOMR: an automatic processing program system for the molecular replacement method"; Journal of Applied Crystallography; vol. 24, pt 6 pp. 1063–1066; Dec. 1991.

Tsuge, H. et al; "Angular distribution of sputtered atoms from polycrystalline metal targets"; J. of Applied Phy. vol. 52, No. 7, pp. 4391–4395; Jul. 1981.

Primary Examiner—James P. Trammell
Assistant Examiner—Kamini Shah

[57] ABSTRACT

A method of determining a space group corresponding to a crystal structure includes a first step of reading a data structure of a target crystal. The data corresponding to the target crystal structure is then compared with data of crystal structures stored in memory. The stored crystal structures are classified according to lattice constants and other conditions. A plurality of space groups included in the crystal system are obtained by extraction from the memory region. An arithmetic operation is performed on the lattice coordinates of each atom constituting the structure (unit cell) of the target crystal by way of matrices corresponding to the space groups to determine equivalent positions of each atom. Each of the obtained crystal structures is then compared with the target crystal. Upon completion of a successful comparison, a description of a target crystal is obtained.

3 Claims, 20 Drawing Sheets

| | CONDITIONS OF LATTICE CONSTANTS | CRYSTAL SYSTEM | SPACE GROUP No. | No. OF MATRICES |
|---|---|---|---|---|
| ① | $a=b=c$<br>$\alpha=\beta=\gamma=90°$ | Cubic | 230 ~195 | 1284 |
| ② | $a=b$<br>$\alpha=\beta=90°$<br>$\gamma=120$ | Hexagonal | 194 ~168 | 330 |
| ③ | $a=b=c$<br>$\alpha=\beta=\gamma$ | Trigonal | 167 ~143 | 225 |
| ④ | $a=b$<br>$\alpha=\beta=\gamma=90°$ | Tetragonal | 142 ~75 | 864 |
| ⑤ | $\alpha=\beta=\gamma=90°$ | Orthorhombic | 74 ~16 | 388 |
| ⑥ | $\alpha=\gamma=90°$<br>OR<br>$\alpha=\beta=90°$ | Monoclinic | 15 ~3 | 172 |
| ⑦ | NONE | Triclinic | 2 ~1 | 3 |

FIG. 3

✡ INPUT DATA $a = 1.0, \quad b = 1.5, \quad c = 2.0$ $\alpha = 87.0, \quad \beta = 92.0, \quad \gamma = 110.0$ $L = 2$ $$A_1(C_1) = \begin{bmatrix} 0.1 \\ 0.1 \\ 0.1 \\ 1.0 \end{bmatrix} \quad A_2(C_2) = \begin{bmatrix} 0.9 \\ 0.9 \\ 0.9 \\ 1.0 \end{bmatrix}$$

| SPACE GROUP NO. | SYMBOLS (NO. OF MATRICES) | | | | | | NO. OF SPACE GROUPS |
|---|---|---|---|---|---|---|---|
| 230 ⎫<br>⎬<br>195 | IA3-D (48) ⎫<br>⎬<br>P23 (12) | | | | | | 36 |
| 194 ⎫<br>⎬<br>168 | P63/MMC (24) ⎫<br>⎬<br>P6 (12) | | | | | | 27 |
| 167 ⎫<br>⎬<br>143 | R3-C (12)    R3-C$ (12)<br><br>P9 (3) | | | | | | 25 |
| 142 ⎫<br>⎬<br>75 | I41/ACD (16)    I41/ACD$ (16)<br><br>P4 (4) | | | | | | 68 |
| 74 ⎫<br>⎬<br>16 | IMMA (8)<br><br>P222 (4) | | | | | | 59 |
| 15 | C2/C (4) | A2/N (4) | I2/A (4) | A2/A$ (4) | B2/N$ (4) | I2/B (4) | |
| 14 | P21/C (4) | P21/N (4) | P21/A (4) | P21/A$ (4) | P21/N$ (4) | P21/B (4) | |
| 13 | P2/C (4) | P2/N (4) | P2/A (4) | P2/A$ (4) | P2/N$ (4) | P2/B (4) | |
| 12 | C2/M (4) | A2/M (4) | I2/M (4) | A2/M$ (4) | B2/M (4) | I2/M$ (4) | |
| 11 | P21/M (4) | P21/M$ (4) | | | | | |
| 10 | P2/M (4) | P2/M$ (4) | | | | | |
| 9 | CC (2) | AN (2) | IA (2) | AA (2) | BN (2) | IB (2) | |
| 8 | CM (2) | AM (2) | IM (2) | AM$ (2) | BM (2) | IM$ (2) | |
| 7 | PC (2) | PN (2) | PA (2) | PA$ (2) | PN$ (2) | PB (2) | |
| 6 | PM (2) | PM$ (2) | | | | | |
| 5 | C2 (2) | A2 (2) | I2 (2) | A2$ (2) | B2 (2) | I2$ (2) | |
| 4 | P21 (2) | P21$ (2) | | | | | |
| 3 | P2 (2) | P2$ (2) | | | | | 13 |
| 2 | P1- (2) | | | | | | |
| 1 | P1 (1) | | | | | | 2 |

MATRICES OF SPACE GROUP No. 4  (MONOCLINIC)

P21: $\begin{pmatrix} 1 & 0 & 0 & 0 \\ 0 & 1 & 0 & 0 \\ 0 & 0 & 1 & 0 \\ 0 & 0 & 0 & 1 \end{pmatrix}, \begin{pmatrix} -1 & 0 & 0 & 0 \\ 0 & 1 & 0 & ½ \\ 0 & 0 & -1 & 0 \\ 0 & 0 & 0 & 1 \end{pmatrix}$  P21\$: $\begin{pmatrix} 1 & 0 & 0 & 0 \\ 0 & 1 & 0 & 0 \\ 0 & 0 & 1 & 0 \\ 0 & 0 & 0 & 1 \end{pmatrix}, \begin{pmatrix} -1 & 0 & 0 & 0 \\ 0 & -1 & 0 & 0 \\ 0 & 0 & 1 & ½ \\ 0 & 0 & 0 & 1 \end{pmatrix}$ MATRICES OF SPACE GROUP No. 3  (MONOCLINIC)

P2: $\begin{pmatrix} 1 & 0 & 0 & 0 \\ 0 & 1 & 0 & 0 \\ 0 & 0 & 1 & 0 \\ 0 & 0 & 0 & 1 \end{pmatrix}, \begin{pmatrix} -1 & 0 & 0 & 0 \\ 0 & 1 & 0 & 0 \\ 0 & 0 & -1 & 0 \\ 0 & 0 & 0 & 1 \end{pmatrix}$  P2\$: $\begin{pmatrix} 1 & 0 & 0 & 0 \\ 0 & 1 & 0 & 0 \\ 0 & 0 & 0 & 1 \\ 0 & 0 & 0 & 1 \end{pmatrix}, \begin{pmatrix} -1 & 0 & 0 & 0 \\ 0 & -1 & 0 & 0 \\ 0 & 0 & 0 & 1 \\ 0 & 0 & 0 & 1 \end{pmatrix}$ MATRICES OF SPACE GROUP No. 2  (TRICLINIC)

P1-: $\begin{pmatrix} 1 & 0 & 0 & 0 \\ 0 & 1 & 0 & 0 \\ 0 & 0 & 1 & 0 \\ 0 & 0 & 0 & 1 \end{pmatrix}, \begin{pmatrix} -1 & 0 & 0 & 0 \\ 0 & -1 & 0 & 0 \\ 0 & 0 & -1 & 0 \\ 0 & 0 & 0 & 1 \end{pmatrix}$ MATRICES OF SPACE GROUP No. 1  (TRICLINIC)

P1: $\begin{pmatrix} 1 & 0 & 0 & 0 \\ 0 & 1 & 0 & 0 \\ 0 & 0 & 1 & 0 \\ 0 & 0 & 0 & 1 \end{pmatrix}$

$$M_1 = \begin{bmatrix} 1 & 0 & 0 & 0 \\ 0 & 1 & 0 & 0 \\ 0 & 0 & 1 & 0 \\ 0 & 0 & 0 & 1 \end{bmatrix} \quad M_2 = \begin{bmatrix} -1 & 0 & 0 & 0 \\ 0 & -1 & 0 & 0 \\ 0 & 0 & -1 & 0 \\ 0 & 0 & 0 & 1 \end{bmatrix}$$

P1 :

$$M_1 = \begin{bmatrix} 1 & 0 & 0 & 0 \\ 0 & 1 & 0 & 0 \\ 0 & 0 & 1 & 0 \\ 0 & 0 & 0 & 1 \end{bmatrix}$$

FIG. 9(A)

EQUIVALENT POSITIONS OBTAINED
BY 1ST SPACE GROUP P1-

$$X_1' = [A_1' \quad A_2'] = \begin{pmatrix} 0.1 & 0.9 \\ 0.1 & 0.9 \\ 0.1 & 0.9 \\ 1.0 & 1.0 \end{pmatrix}$$
$(M_1)$

FIG. 9(B)

$$X_2' = [A_1' \quad A_2'] = \begin{pmatrix} 0.9 & 0.1 \\ 0.9 & 0.1 \\ 0.9 & 0.1 \\ 1.0 & 1.0 \end{pmatrix}$$
$(M_2)$

NOT REGISTERED INTO ATOM LIST

FIG. 9(C)

EQUIVALENT POSITIONS OBTAINED
BY 2ND SPACE GROUP P1

$$X_1' = [A_1' \quad A_2'] = \begin{pmatrix} 0.1 & 0.9 \\ 0.1 & 0.9 \\ 0.1 & 0.9 \\ 1.0 & 1.0 \end{pmatrix}$$
$(M_1)$

FIG. 10(A)

EQUIVALENT POSITIONS OBTAINED
BY 1ST SPACE GROUP P1-

$$X_1' = [A_1' \quad A_2'] = \begin{pmatrix} 0.1 & 0.9 \\ 0.1 & 0.9 \\ 0.1 & 0.9 \\ 1.0 & 1.0 \end{pmatrix}$$
$(M_1)$

FIG. 10(B)

EQUIVALENT POSITIONS OBTAINED
BY 2ND SPACE GROUP P1

$$X_1' = [A_1' \quad A_2'] = \begin{pmatrix} 0.1 & 0.9 \\ 0.1 & 0.9 \\ 0.1 & 0.9 \\ 1.0 & 1.0 \end{pmatrix}$$
$(M_1)$

TABLE OF SPACE-GROUP FOUND

| SPACE GROUP No. | SPACE GROUP SYMBOL |
|---|---|
| 1 | P 1 |
| 2 | P 1- |

FIG. 11

| TABLE OF SPACE-GROUP FOUND | |
|---|---|
| SPACE GROUP No. | SPACE GROUP SYMBOL |
| 8 5 | P 4 / N $ |
| 1 2 9 | P 4 / N M M $ |

FIG. 19

METHOD OF DETERMINING A SPACE GROUP

BACKGROUND OF THE INVENTION (1) Field of the Invention

This invention relates to a method of determining a space group descriptive of a structure of a crystal.

(2) Description of the Related Art

In designing a functional material, such as a superconductor or a semiconductor, it is an indispensable work to first form a model of a crystal structure of a material on the level of atoms, and then extract data of the crystal structure from the model. A particularly important factor of high efficiency of this work is to determine, at a high speed, a space group descriptive of the crystal structure of the material, which forms the most important element of all data concerning the crystal structure, and therefore, a method has been demanded which makes it possible to determine a space group descriptive of the crystal structure of a material at such a high speed.

Conventionally, modeling of a crystal structure is performed by putting together plastic parts into a three-dimensional model, and then tracing the structure of this model. Therefore, the determination of a space group from such an imaginary crystal structure is mainly performed as a manual work on the desk.

Further, recently, in designing an organic material, a molecular design support system based on the use of isolated molecular systems has been developed. The molecular design support system, however, is not applied to handling of an organic material, such as a superconductor, on the level of crystals (on the level of collective molecular systems), and hence clarification of complicated functional characteristics of such a material in designing same is also manually performed by the use of plastic models.

As described above, in the state of the art, the manual work cannot be avoided in the determination of a space group descriptive of a crystal structure, and hence the whole process up to the determination of the space group is an inefficient one, requiring a very time-consuming labor.

Further, it is difficult to realize a crystal structure having a complicated spatial arrangement by assembling a model by the use of plastic parts. Further, in realizing a complicated crystal structure with a high symmetry (symmetricalness), there arises a problem of liability to a human error, such as an erroneous omission of data.

SUMMARY OF THE INVENTION

The present invention has been made in view of these circumstances, and it is the object of the invention to provide a method of determining a space group, which enables the work of determining the space group to be performed with efficiency.

To attain the above object, the present invention provides a method of determining a space group descriptive of a structure of a crystal. The method of determining a space group according to the invention comprises determining a crystal system to which a structure of a target crystal belongs, performing packing processing by the use of a plurality of space groups included in the crystal system, and performing comparison between each of a plurality of crystal structures obtained by the packing processing and the structure of the target crystal, and determining, when one of the plurality of crystal structures obtained from a corresponding one of the plurality of space groups by the packing processing agrees with the structure of the target crystal, that the corresponding one of the plurality of space groups is one descriptive of the structure of the target crystal.

The above and other objects, features and advantages of the present invention will become apparent from the following description when taken in conjunction with the accompanying drawings which illustrate preferred embodiments of the present invention by way of example.

BRIEF DESCRIPTION OF THE DRAWINGS

FIG. 3 is a table showing a classification of crystal systems;

FIG. 5 is a diagram showing input data of the target crystal;

FIG. 6 is a table showing an excerpt from a list of space groups divided into sections corresponding to respective crystal systems and symbols for each of the space groups;

FIG. 7 is a diagram showing an excerpt from a list of matrices corresponding to space groups;

FIG. 8 is a diagram showing matrices corresponding to space groups of a triclinic system;

FIGS. 9(A), 9(B), and 9(C) are diagrams for explaining a step of packing processing;

FIGS. 10(A) and 10(B) are diagrams showing final results of the packing processing;

FIG. 11 is a diagram showing how data of determined space groups is presented on a display;

FIG. 19 is a diagram showing how data of determined space groups is presented on a display.

DESCRIPTION OF THE PREFERRED EMBODIMENT

First, an outline of an embodiment of the invention will be described.

Figure 1:
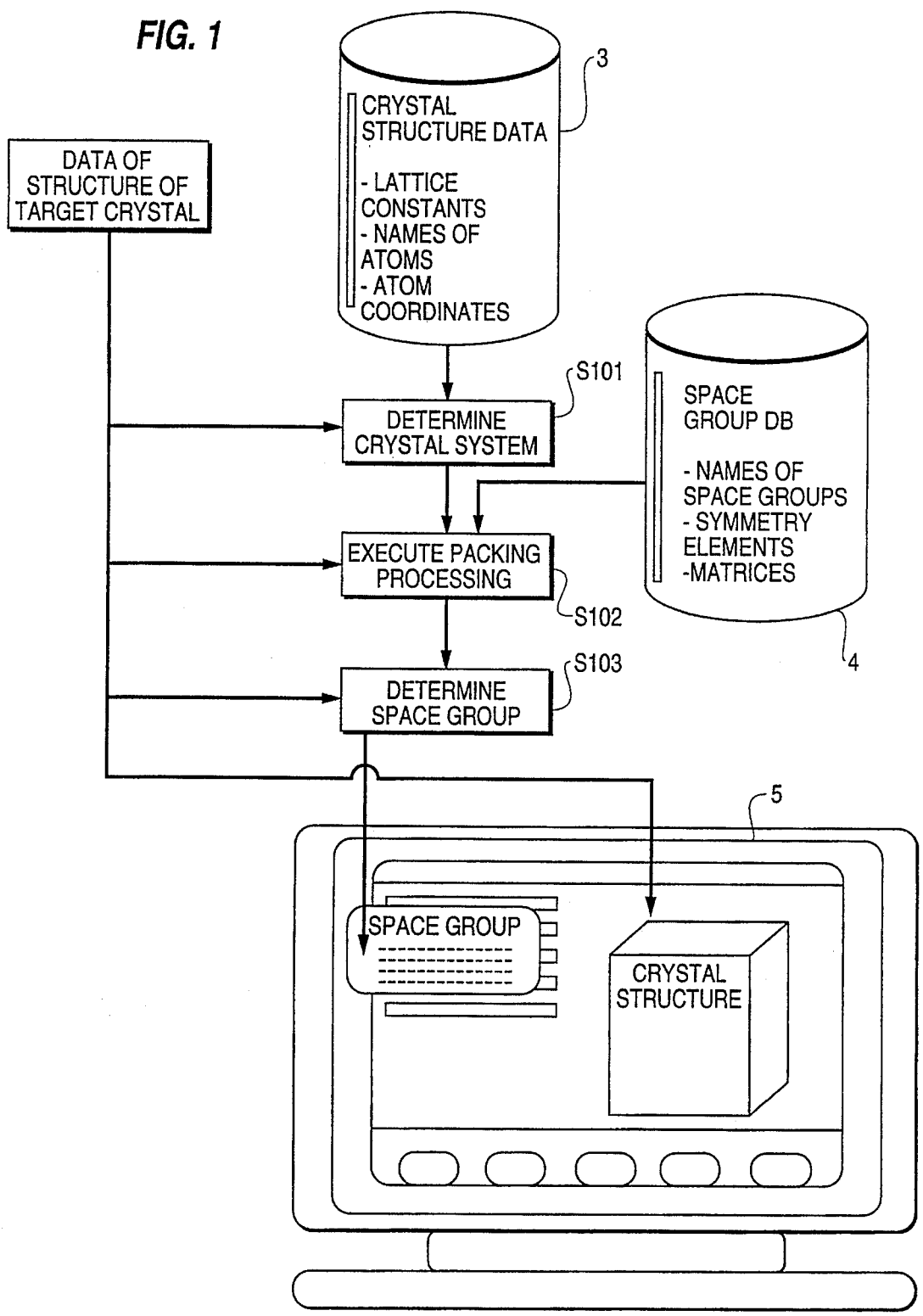
FIG. 1 is a diagram which is useful in explaining the principle of the present invention.

Referring first to FIG. 1, an overall procedure of the processing by the method of the present invention will be described. In the figure, reference numerals 3 and 4 designate memory regions formed by external memory devices, such as hard disks. The memory region 3 stores data concerning crystal structures, such as lattice constants, names of atoms, atom coordinates (atom parameters), and the memory region 4 stores data concerning space groups, such as names of space groups, symmetry elements, and matrices for use in the packing processing, described hereinafter.

First, at the step S101, data is read which sets information known of the structure of a target crystal, i.e. a crystal for which a space group descriptive of the structure thereof is to be determined. The data set on the structure of the target crystal includes lattice constants, atom coordinates, names of atoms constituting a unit cell of the target crystal, and so on. The data known of the structure of the target crystal is compared with data of conditions, i.e. lattice constants, classifying crystal structures into categories of crystal systems, which are stored in advance in the memory region 3, to thereby determine a crystal system to which the target crystal belongs. A manner of determination of the crystal system will be described hereinafter in detail with reference to FIG. 2 and FIG. 3. Further, an image of the crystal structure formed from the input data known of the structure of the target crystal is presented on the right side of the display 5, as shown in FIG. 1.

Then, space groups included in the crystal system determined at the step S101 are read from the memory region 4, and the space groups are sequentially used in the packing processing at the step S102. More specifically, matrices corresponding to each of the space groups thus determined are used to perform arithmetic operations on the atom coordinates of each of the atoms constituting a unit cell of the structure of the target crystal to determine equivalent positions of each atom. Details of this processing will be described hereinbelow.

Then, at the step S103, each of a plurality of crystal structures obtained by the above packing processing is sequentially compared with the structure of the target crystal, and when the crystal structure obtained from the space group by the packing processing agrees with the structure of the target crystal, it is determined that the space group is one descriptive of the structure of the target crystal. Details of the process will be described hereinbelow. Data of space groups thus determined is presented on the left side of the display 5.

Figure 2:
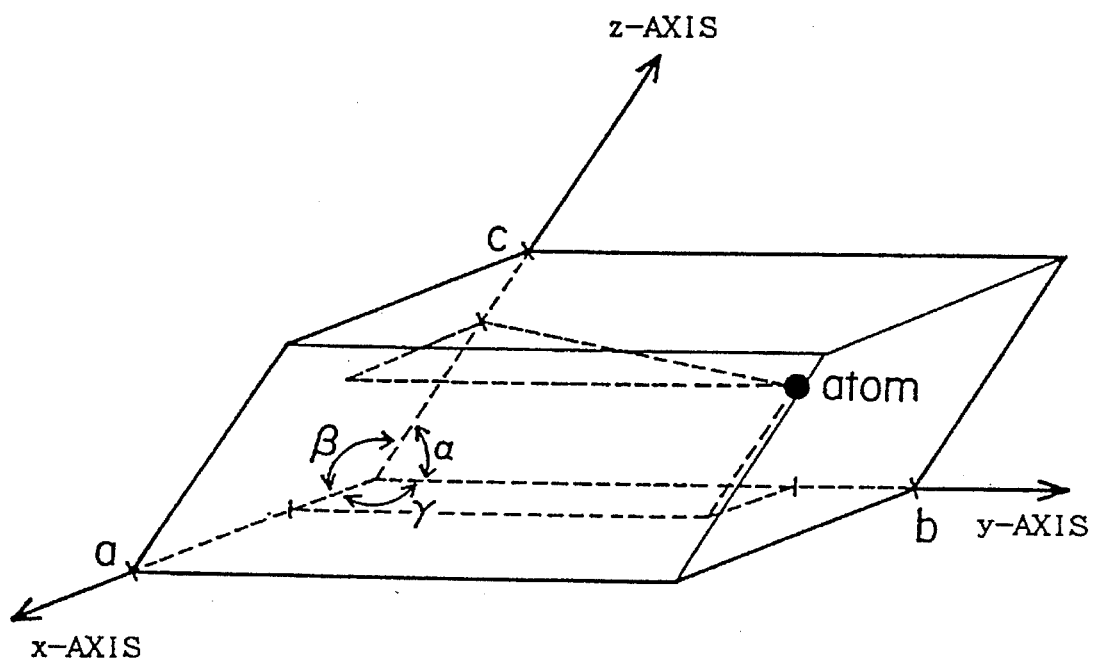
FIG. 2 is a diagram which is useful for explaining the definition of a unit cell of a crystal structure.

FIG. 2 is a diagram which is useful in explaining the definition of a unit cell of a crystal structure. A unit cell as a basis of a crystal structure contains atoms within a volume of space defining the unit cell as a parallelepiped having three axes of x, y, and z as shown in the figure. The parallelepiped of the unit cell is defined by six parameters of lattice constants, i.e. axial length elements of a, b and c, and angle elements $\alpha$, $\beta$, and $\gamma$ each formed between two of the axes.

FIG. 3 is a table showing a classification of crystal systems. Features of crystal structures can be determined by numerical values of the lattice constants shown in FIG. 2, and classified into seven categories of crystal systems as shown FIG. 3. Each crystal system includes or corresponds to a plurality of space groups, for each of which are defined matrices correspondent thereto. For example, a cubic system (Cubic) includes space groups No. 195 to No. 230, with 1284 matrices defined therefor in a manner corresponding to the space groups No. 195 to No. 230.

A crystal system has stricter conditions as the symmetry (symmetricalness) thereof is higher, i.e. as a row of data therefor is positioned higher in the FIG. 3 table. In general, one crystal structure can belong to a plurality of crystal systems, and therefore it is required to select one having the highest symmetricalness among them. Accordingly, in the present embodiment, the lattice constants of the target crystal are sequentially compared with those of a crystal system having the highest symmetricalness toward those of one having the lowest symmetricalness, and a first crystal system found to have conditions in agreement with those of the target crystal is determined to be a desired one.

This procedure of determining the crystal system permits reduction of the number of items to be searched, whereby it is made possible to determine a crystal system at a high speed. In this connection, the basic data shown in FIG. 3 (data of crystal structures), which has been stored in the memory region 3 in advance, is read and used in determination of the crystal system as mentioned hereinabove.

Next, details of the procedure of packing processing and space group-determining processing will be described with reference to FIG. 4 to FIG. 9.

Figure 4:
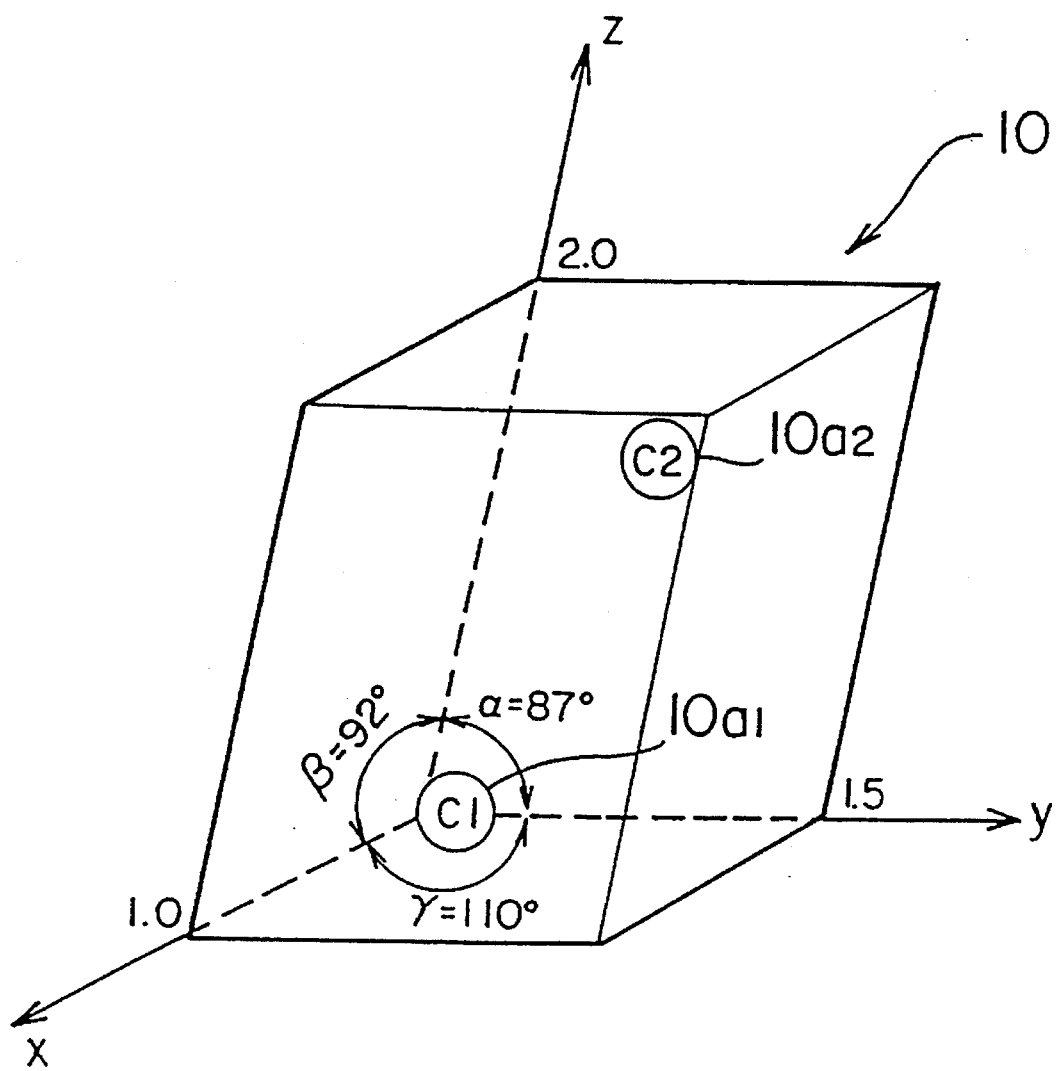
FIG. 4 is a diagram showing a structure of a crystal as a target (target crystal)

FIG. 4 shows the structure of a target crystal 10 on which a space group is to be determined this time. The unit cell of the crystal 10 is comprised of two carbon atoms $10a_1$ and $10b_2$. The name of the atom $10a_1$ is represented by "C1" and that of the atom $10a_2$ by "C2".

FIG. 5 shows input data of the crystal 10 appearing in FIG. 4. In the figure, a, b, c, $\alpha$, $\beta$, and $\gamma$ designate the lattice constants, $A_1$ designates the atom coordinates of the atom $10a_1$ (C1) in the unit cell, $A_2$ those of the atom $10a_2$ (C2), and L the number of atoms contained in the unit cell. The input data of the crystal 10 is prepared in advance and stored into a predetermined memory region.

In the packing processing, as described hereinabove, the crystal system to which the crystal 10 belongs is determined based on the input data shown in FIG. 5 by the use of the FIG. 3 table. The determination of the crystal system is performed by checking the input data with the conditions of the lattice constants shown in the FIG. 3 table in the order of the highest symmetricalness toward the lowest one. In the present example, a condition of $a \neq b \neq c$ is satisfied for the axial length elements a, b, and c, and one of $\alpha \neq \beta \neq \gamma \neq 90°$ for the rotational angles $\alpha$, $\beta$, and $\gamma$ representative of angles each formed between two of the axes. Therefore, the crystal system corresponding thereto is determined to be a triclinic which is lowest in symmetricalness. Accordingly, it is determined that the crystal 10 is triclinic, and then the space groups included in the triclinic system are used in the packing processing.

Now, referring to FIG. 6 and FIG. 7, matrices corresponding to the space groups will be described.

FIG. 6 shows an excerpt from a table of space groups corresponding to each crystal system, and symbols therefor. The space groups can be classified by the use of Hermann-Mauguin's symbols as shown in the FIG. 6. In this connection, the number of space groups for each crystal system is shown on the right end column of the figure. Further, there are matrices defined in a manner corresponding to each of the space groups. The number of matrices for each space group is designated within a parenthesis affixed to the rear of each symbol. For example, in FIG. 6, Space Group No. 4 consists of two kinds of space groups P21 and P21$ in terms of Hermann-Maguin's symbols, with two matrices being defined for each kind of the space groups P21 and P21$.

FIG. 7 shows matrices corresponding to Space Groups No. 4 to No. 1. The crystal 10 as the present target crystal has been determined, as described hereinabove, to be the triclinic system (⑦ in the FIG. 3 table), which corresponds to Space Groups No. 2 and No. 1, as shown therein. Therefore, the symbols for the space groups of the present target crystal are P1 and P1- as shown in FIG. 6. In this connection, the symbol "-" of "P1-" represents an axis of rotation-inversion. In correspondence to the space group P1-, two matrices are defined as shown in FIG. 7. Further, in correspondence to the space group P1, one matrix is defined. The data of space groups and matrices corresponding thereto are stored in the memory region 4, as described hereinabove.

FIG. 8 shows the results of extraction of matrices corresponding to the possible space groups descriptive of the target crystal, from the data of space groups the excerpt of which is shown in FIG. 7. The packing processing is performed by the use of the matrices $M_1$ and $M_2$ corresponding to the space group P1-, and the matrix $M_1$ corresponding to P1. More specifically, the symmetry operation is conducted by carrying out arithmetic operation on the atom coordinates $A_1$ and $A_2$ of the input data shown in FIG. 5 by the use of these matrices to thereby determine the coordinates of equivalent positions of the atoms $10a_1$ and $10a_2$.

FIGS. 9(A), 9(B), and 9(C) is for explaining a step of the packing processing. In this figure, $X_1'=[A_1' A_2']$ for a first space group (Space Group No. 2) P1- shows results of an arithmetic operation by the use of the matrix $M_1$, while $X_2'=[A_1' A_2']$ for same those of an arithmetic operation by the use of the matrix $M_2$. $X_1'=[A_1' A_2']$ for a second space group (Space Group No. 1) P1 shows results of an arithmetic operation by the use of the matrix $M_1$. $A_1'$ and $A_2'$ are the coordinates of equivalent positions of the atoms $10a_1$(C1) and $10a_2$(C2). The results of arithmetic operation $X_1'$ obtained by the use of the matrix $M_1$ of the first space group P1- and those $X_2'$ by the use of the matrix $M_2$ thereof are opposite to each other in respect of the coordinates $A_1'$ and the coordinate $A_2'$ of equivalent positions. The atom $10a_1$ and the atom $10a_2$ in the present case are both carbons (C), i.e. identical to each other, and hence, after all, the results $X_1'$ by the matrix $M_1$ and the results $X_2'$ by the matrix $M_2$ overlap each other, i.e. are duplicate. To avoid this overlapping or duplication, the results by the matrix $M_2$ are canceled, and are not registered into an atom list. Final results of the arithmetic operations of the packing processing are shown in FIGS. 10(A) and 10(B).

The determination of a space group descriptive of the target crystal is performed by the use of the final results of the above packing processing. More specifically, the input data shown in FIG. 5 is checked with the results of the packing processing shown in FIGS. 10(A) and 10(B) to determine whether they agree with each other in respect of the number of atoms, the atom coordinates, and the name of atoms. In the present case, with both of the first and second space groups P1- and P1, the number of atoms, the atom coordinates, and the name of atoms obtained by the packing processing agree with those of the input data. Therefore, both the space groups P1- and P1 are determined to be ones descriptive of the structure of the crystal 10. The results of determination of the space groups are presented on the display 5 as described hereinabove. FIG. 11 shows details of the presentation.

Figure 12:
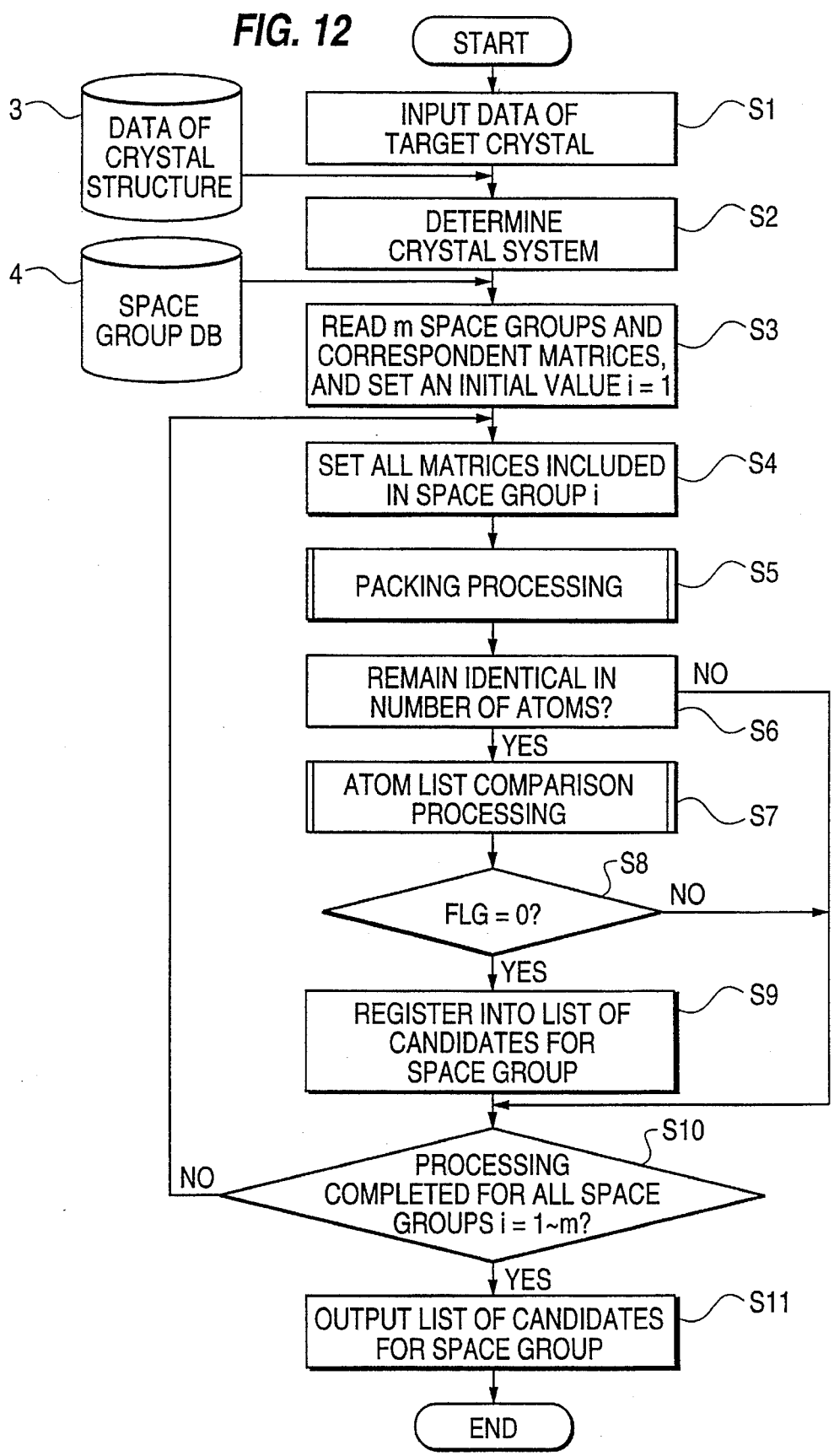
FIG. 12 is a flowchart of an overall program for executing the packing processing and the space group-determining processing.
Figure 13:
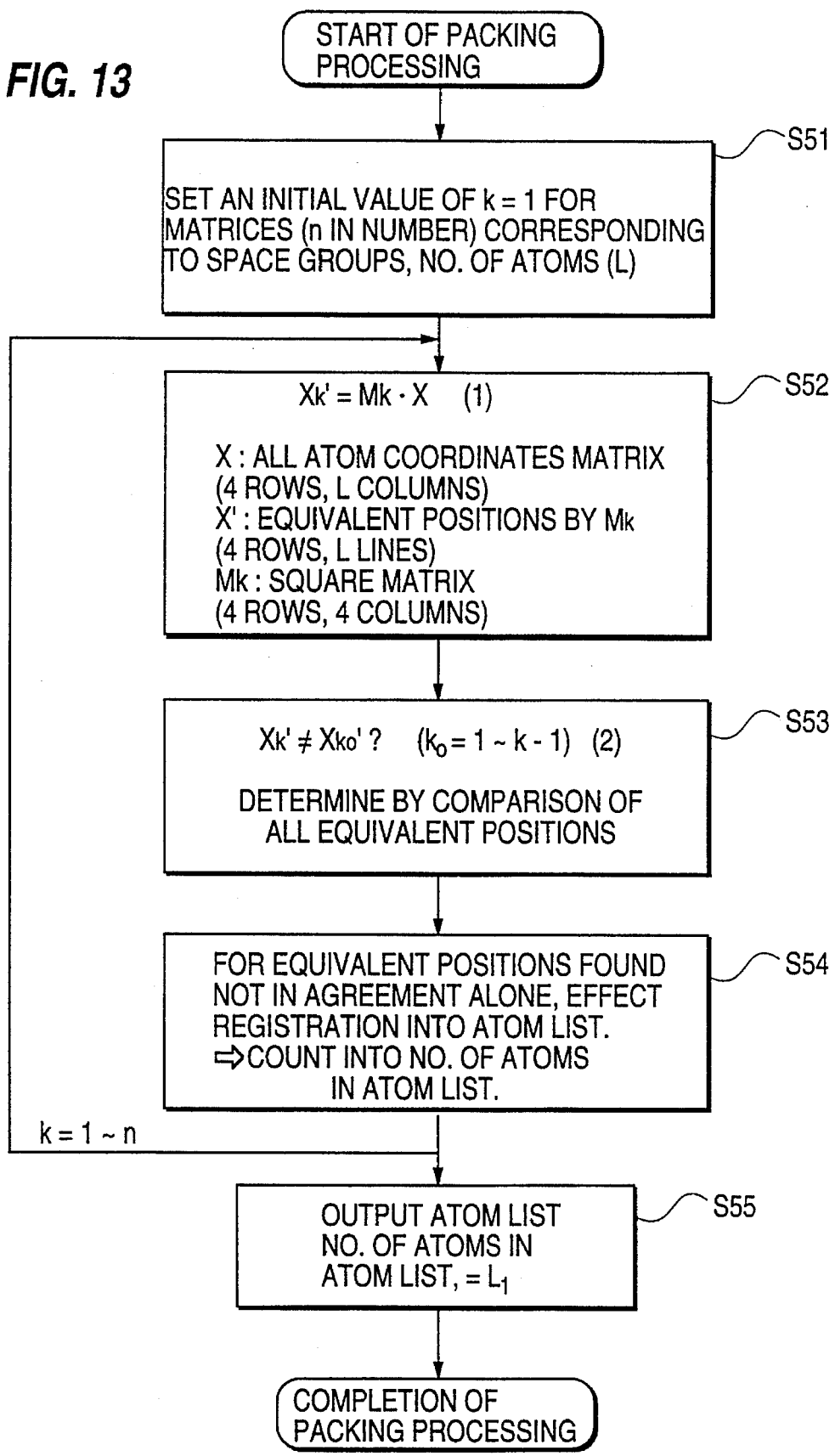
FIG. 13 is a flowchart of a program for executing the packing processing.
Figure 14:
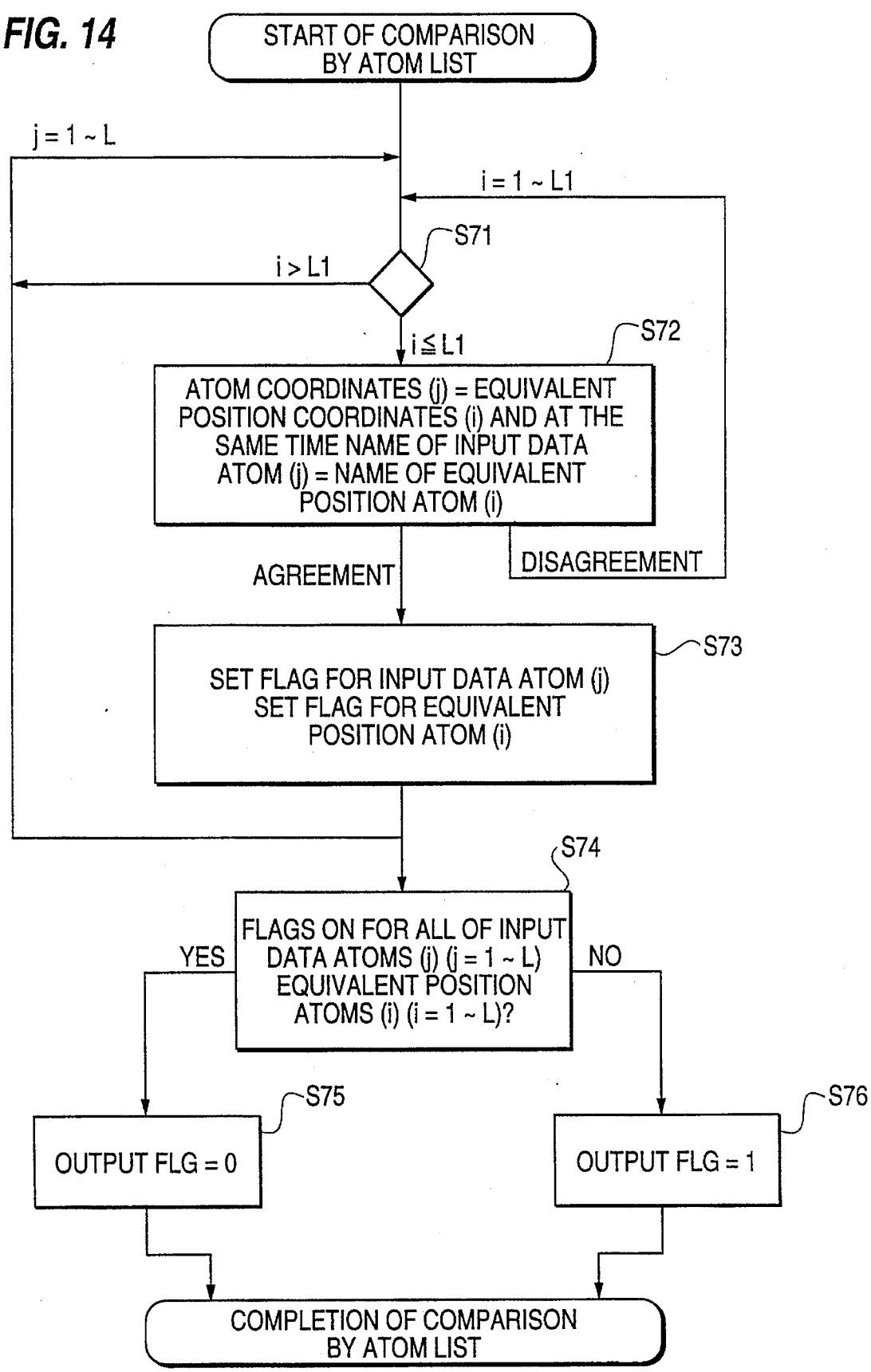
FIG. 14 is a flowchart showing a procedure of the space group-determining processing.

FIG. 12, FIG. 13 and FIG. 14 show programs for executing the packing processing and space group determining processing. FIG. 12 shows an overall program for executing the above processings, while FIG. 13 shows a program for the packing processing, and FIG. 14 a program for the space group-determining processing. In these figures, each reference numeral formed of a character S and a number following it designates a step number.

[S1] The data of a crystal structure of an target crystal is input. In the example described above, the input data of the crystal 10 shown in FIG. 5 is read by the computer.

[S2] A crystal system of the target crystal is determined based on the data of crystal structures stored in the memory region 3. This determination is performed by searching the data (shown in FIG. 3) concerning the crystal systems stored in the memory region 3 in the order of the highest symmetricalness toward the lowest one. In the case of the input data of the crystal 10 shown in FIG. 5, the relationship or condition of a≠b≠c excludes crystal systems ① to ④ shown in FIG. 3, and the relationship or condition of α≠β≠ excludes crystal systems ⑤ and ⑥, and hence the system of the crystal system is determined to be triclinic.

[S3] Matrices corresponding to the space groups (P1, P1- in the FIG. 5 case) included in the crystal system (triclinic in same) are read out from the data of the space groups stored in the memory region 4.

[S4] All the matrices ($M_1$ and $M_2$ of P1-, and $M_1$ of P1 in the FIG. 5 case) which belong to the i-th space group are set.

[S5] Packing processing is performed by the use of the matrices corresponding to the i-th space group. Details thereof will be described hereinbelow with reference to FIG. 13.

[S6] It is determined whether or not the packing processing has given an identical number of atoms. More specifically, it is determined whether or not the number L of atoms set in the input data (in the FIG. 5 case, two; atoms $10a_1$ and $10a_2$) is equal to the number $L_1$ of atoms obtained by the packing processing and registered in the atom list (the total number of atoms determined from registered results $X_1'$, $X_2'$, etc. of the arithmetic operations in FIG. 9). If the answer to this question is affirmative (YES), the program proceeds to a step S7, whereas if the answer is negative (NO), the program jumps over to a step S10.

[S7] Comparison processing (for determining a space group) by the use of the atom list is performed. That is, the input data is checked with results of the packing processing to thereby determine the names of atoms and coordinates of equivalent positions (atom coordinates) of atoms. Details of this processing will be described in detail with reference to FIG. 14.

[S8] It is determined whether or not a flag FLG is equal to 0. If the answer to this question is affirmative (YES), the program proceeds to a step S9, whereas if the answer to this question is negative (NO), the program jumps over to the step S10. The flag FLG is set to 0 at a step S75 in FIG. 14 when the comparison processing by the use of the atom list is normally terminated with affirmative results, as will be described in detail hereinafter.

[S9] Since the comparison processing has been normally performed with affirmative results, the space group is registered into a list of candidates of space groups, i.e. determined as one descriptive of the target crystal.

[S10] It is determined whether or not the packing processing has been performed for all the space groups (the number thereof being represented by m). If it is determined that the packing processing of all the space groups is completed, the program proceeds to a step S11. If not completed, the program returns to the step S4.

[S11] The list of candidates of space groups is output for presentation on the display 5 as shown in FIG. 11.

Referring now to FIG. 13, the packing processing at the step S5 in FIG. 12 will be described.

[S51] The affix k to a matrix M corresponding to a space group is set to an initial value of 1.

[S52] By the use of the matrix $M_k$, the equivalent position coordinates (coordinates of equivalent positions) $X_k'$ are calculated for all the atom coordinates X of the target crystal by the use of the following equation (1):

$$X_k' = M_k \cdot X \qquad (1)$$

where X represents a matrix indicative of all the atom coordinates (four rows by L columns) and $X_k'$ the equivalent position coordinates obtained by the matrix $M_k$, which is a square matrix of four rows by four columns.

[S53] It is determined whether or not the equivalent position coordinates thus calculated overlap the equivalent position coordinates having been calculated heretofore. That is, the determination by the use of the following equation (2) is performed with all of the equivalent position coordinates obtained:

$$X_k' \neq X_{ko}' \, (ko=1 \text{ to } k-1) \qquad (2)$$

[S54] Only the equivalent position coordinates determined, by the equation (2), not to be duplicate are additionally registered into the atom list.

[S55] The atom list is output.

Next, the comparison processing by the use of the atom list executed at the step S7 in FIG. 12 will be described with reference to FIG. 14. First, symbols used in FIG. 14 will be described. A small letter j represents a parameter for specifying a set of atom coordinates (i.e. the coordinates of an atom (hereinafter referred to as "input data atom") in a unit cell of the target crystal), and a letter L the number of atoms contained in the unit cell. Further, a small letter i is a parameter for specifying a set of equivalent position coordinates (the coordinates of an atom (hereinafter referred to as an "equivalent position atom") in an equivalent position), and a letter $L_1$ the number of atoms registered in the atom list of the equivalent position coordinates.

[S72] It is determined whether or not an i-th equivalent position atom specified by the specifying parameter i exists at a position of the atom coordinates of a j-th input data atom specified by the specifying parameter j, and at the same time both the equivalent position atom and the input data atom have an identical name.

[S73] A flag is set for indicating that the i-th input data atom and the j-th equivalent position atom agree with each other.

The parameters used at the processing steps S71 to S73 are controlled such that the specifying parameter j is sequentially stepped from 1 to L to thereby perform determination on the atom coordinates of all the input data atoms, and that the specifying parameter i is sequentially stepped from 1 to $L_1$ in relation to the atom coordinates of each of the input data atoms to compare the coordinates of each of the equivalent position atoms with the atom coordinates of the corresponding input data atom. In the course of the comparison, control is performed in a manner dependent on a case where there is an equivalent position atom found in agreement with an input data atom, and a case where there has been no equivalent position atom found in agreement with the input data atom throughout the comparison.

[S74] It is determined whether or not flags have been set for all the input data atoms (by stepping the parameter j from 1 to L), and for all the equivalent position atoms (by stepping the parameter i from 1 to L1),

[S75] A flag FLG=0 is output or set, if the answer to the question of the step S74 is affirmative (YES).

[S76] A flag FLG=1 is output or set if the answer to the question of the step S74 is negative (NO).

Next, an example of structure analysis performed on a crystal by the method of determining a space group of the present invention will be described with reference to FIG. 15 to FIG. 20. Let it be assumed here that a crystal as a target of analysis is one of $LaGdSrCuO_4$. In the case of investigation into such a perovskite-like copper oxide superconductor, it is an effective technique of investigating a new substance to laminate partial structures to grasp a laminate structure characteristic of the substance. The structure analysis of the target crystal by this technique will be described in the following.

Figure 15:
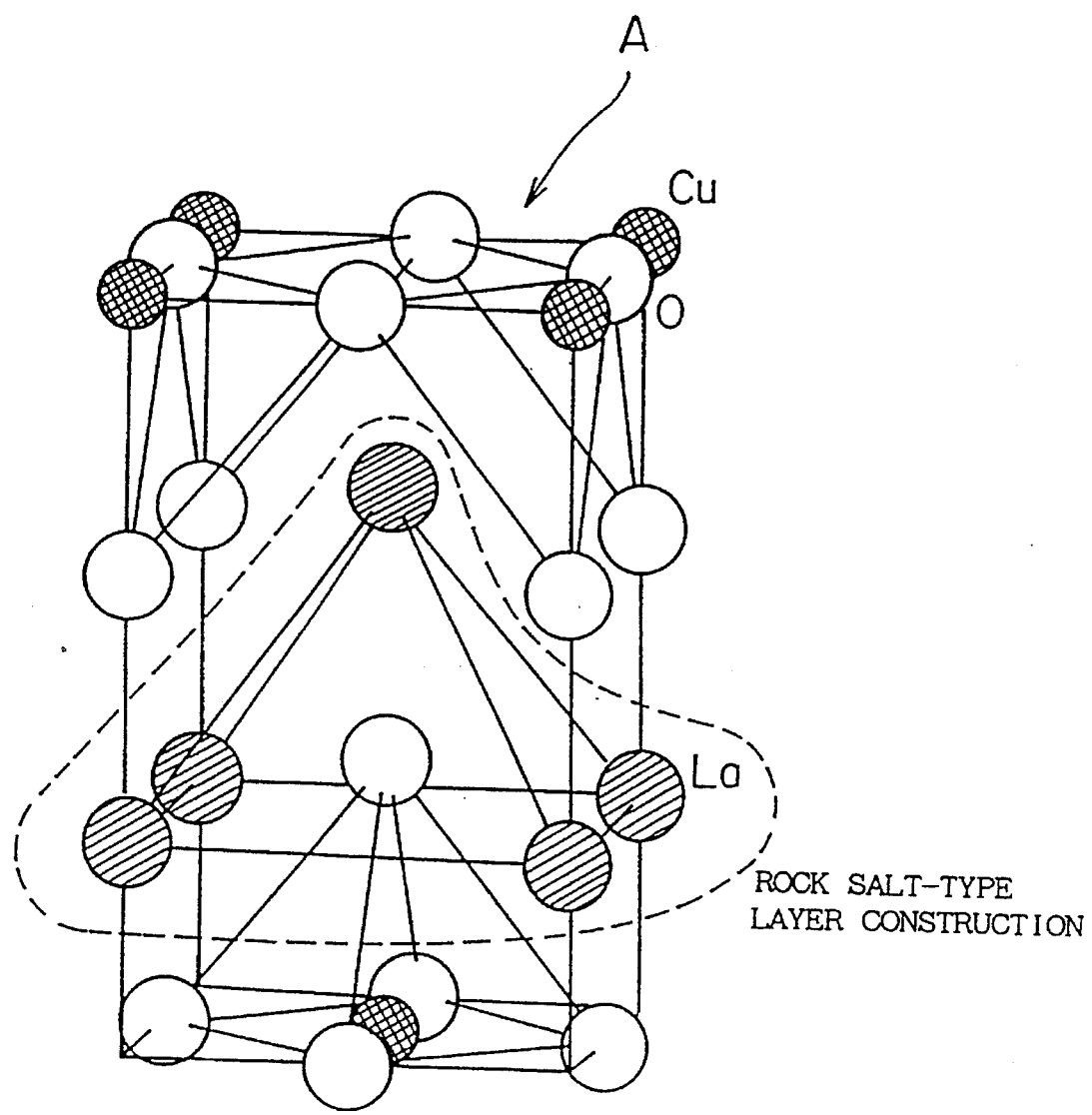
FIG. 15 is a diagram showing a laminate crystal structure.

FIG. 15 shows a laminate crystal structure A. The crystal structure A in this figure is formed by $LaSrCuO_4$, and includes a $La_2O_2$ layer with a rock salt-type structure, and a $CuO_2$ layer sandwiched by adjacent $La_2O_2$ layers. The crystal structure A is stored in advance as a partial structure of a laminated structure.

Figure 16:
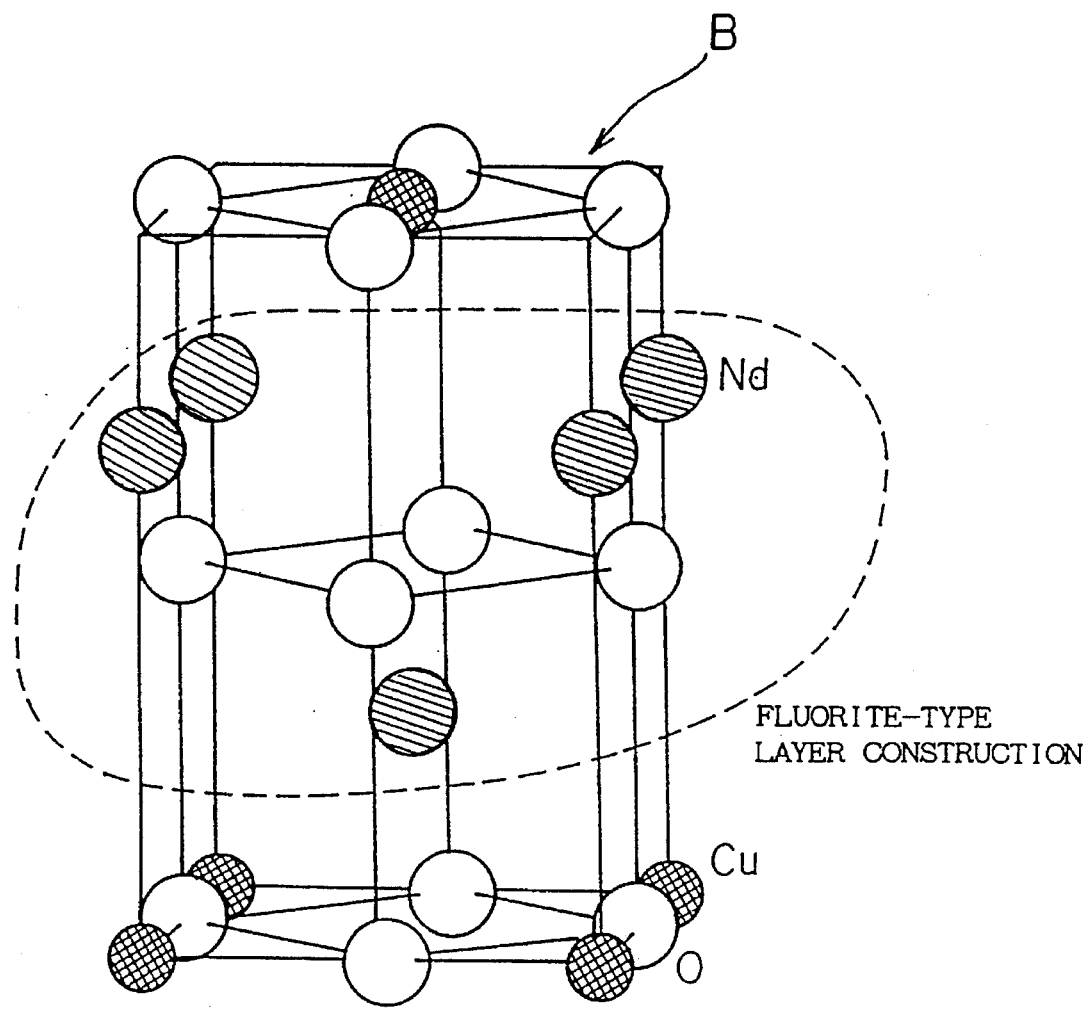
FIG. 16 is a diagram showing a laminate crystal structure.

FIG. 16 shows a laminate crystal structure B. In this figure, the crystal structure B is formed by $Nd_2CuO_4$, and includes a $Nd_2O_2$ layer with a fluorite-type structure, and a $CuO_2$ layer sandwiched by adjacent $Nd_2O_2$ layers. The crystal structure B is stored in advance as a partial structure of the laminated structure.

Figure 17:
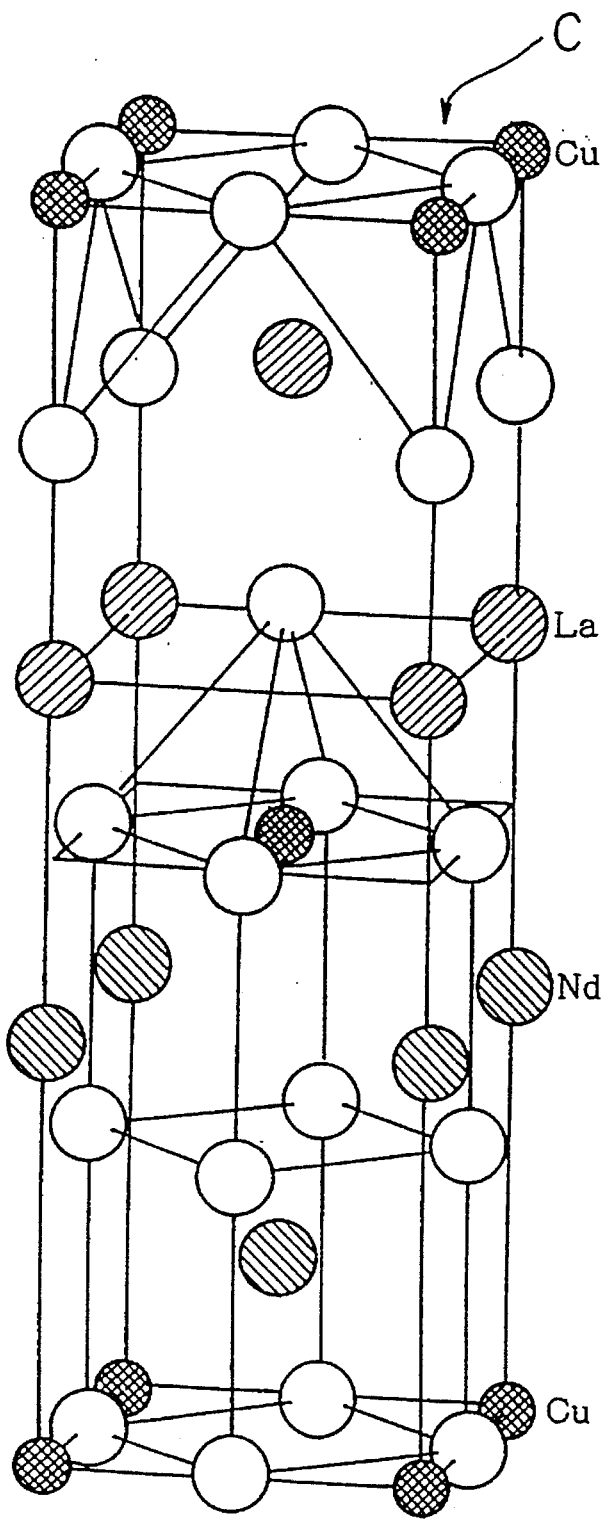
FIG. 17 is a diagram showing an imaginary crystal structure, which is synthesized by superposing one crystal structure upon the other.

It is expected that the crystal structure of $LaGdSrCuO_4$ can be synthesized by superposing the crystal structure A and the crystal structure B one upon the other. The resulting imaginary crystal structure C is shown in FIG. 17. The synthesis of the crystal structures A and B is performed by determining transformation coefficients for transforming the coordinates of each atom of a laminate source into the coordinates of an atom of a resultant laminate, and then performing the transformation based on the transformation coefficients. Concerning the imaginary crystal structure C of FIG. 17, the position of the origin often causes problems, and hence the origin is shifted to a suitable position. A crystal structure obtained by a shift of the origin is shown in FIG. 18.

Figure 18:
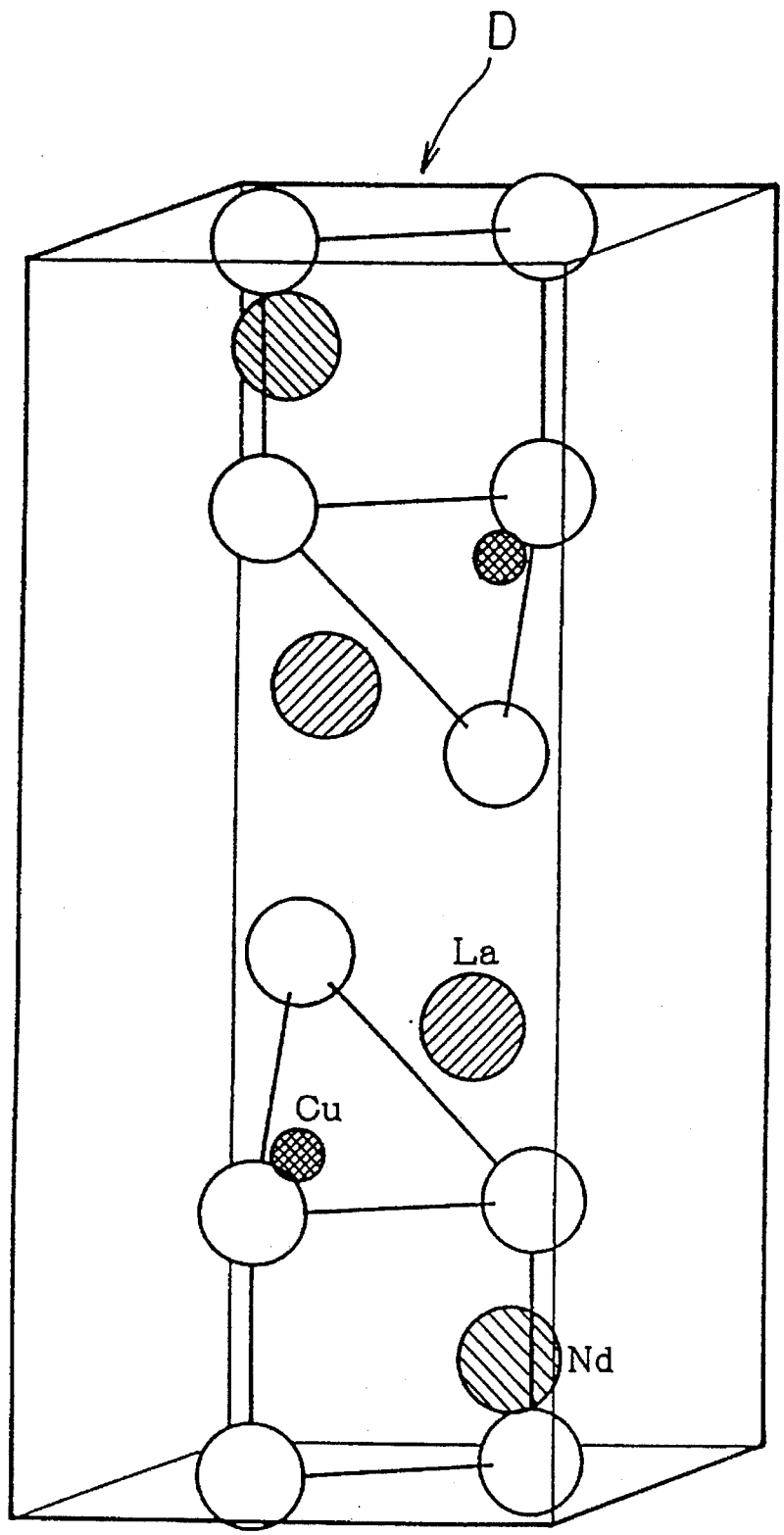
FIG. 18 is a diagram showing a crystal structure obtained by shifting the origin.
Figure 20:
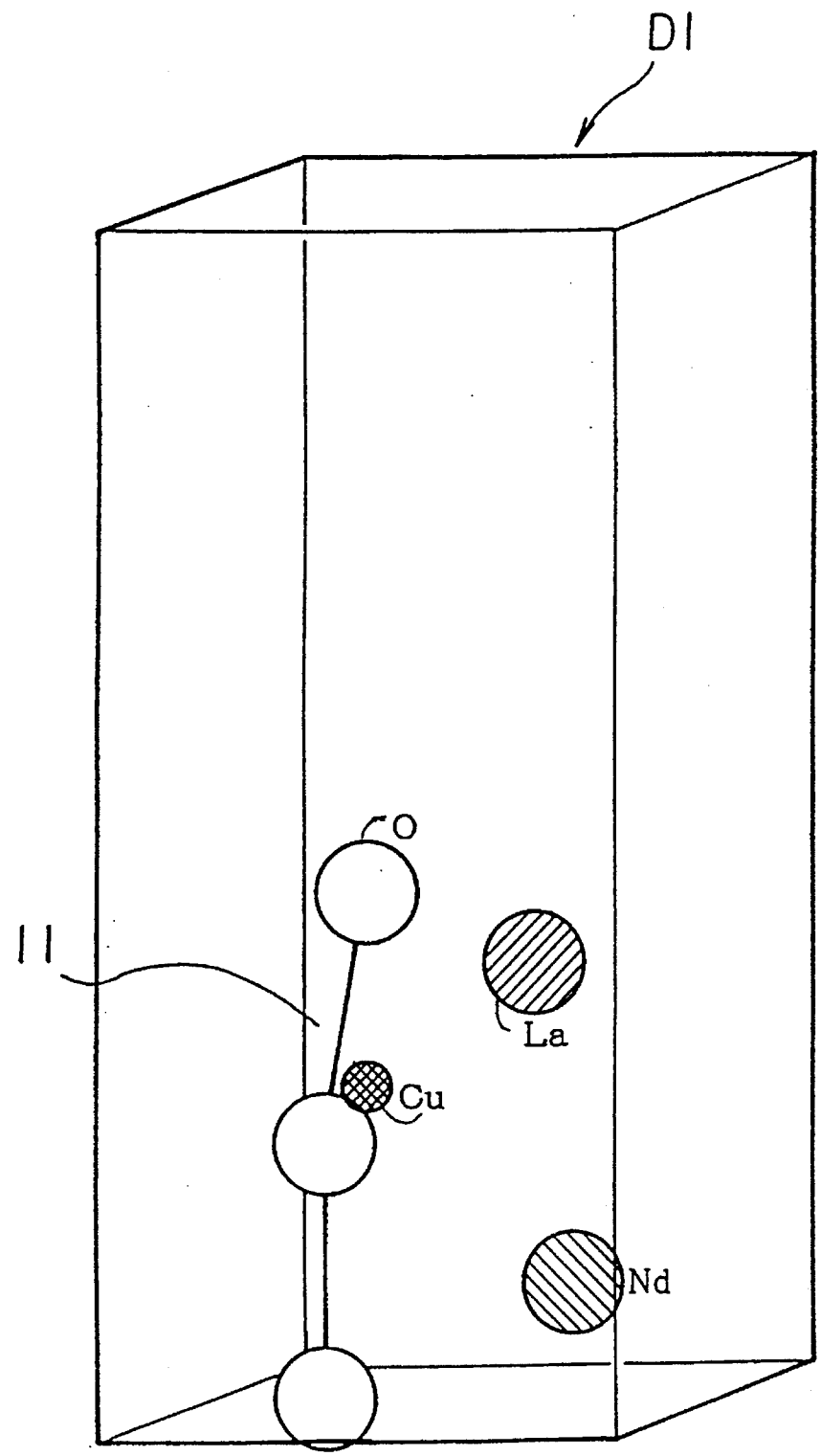
FIG. 20 is a diagram showing a crystal structure depicted by the use of an asymmetric unit.

Then, a space group descriptive of the crystal structure D shown in FIG. 18 is determined according to a procedure of the packing processing and space group-determining processing based on the method of the invention described above. As a result, it is determined that there are two space groups P4/N$ and P4/NMM$ descriptive of the crystal structure D, as shown in FIG. 19. Once the space groups descriptive of the crystal structure D are determined, an asymmetric unit 11 of the crystal structure D can be determined by deleting the atom coordinates of equivalent points from the atom coordinates thereof. A crystal structure $D_1$ depicted by the use of the asymmetric unit 11 is shown in FIG. 20. When the asymmetric unit 11 of the crystal structure is known, it is possible to perform calculation of an X-ray diffraction pattern by utilizing its symmetry by means of a computer.

The calculated diffraction pattern and an actual diffraction pattern obtained by X ray is compared with each other, whereby the structure of the target crystal of $LaGdSrCuO_4$ can be analyzed with a higher accuracy. Further, since the diffraction pattern can be determined by calculation, it is possible to perform the analysis with ease, even for a complicated crystal structure.

As described heretofore, in the present embodiment, a space group is automatically extracted according to the procedure of the packing processing and space group-determining processing. Therefore, a space group, which has been conventionally determined in a trial-and-error manner by assembling a plastic model or by calculation on the desk, can be obtained at a high speed and with high efficiency. Further, even when a space group descriptive of a crystal structure having a high symmetricalness is to be determined, there is no room for occurrence of human errors, and hence the space group can be determined with a high reliability.

As described above, according to the invention, a plurality of crystal structures obtained by the packing processing by the use of space groups are compared with a known structure of a target crystal, and when one of the plurality of crystal structures obtained from a corresponding one of the plurality of space groups agrees with the known structure of the target crystal, the space group is determined to be one descriptive of the structure of the target crystal. This makes it possible to determine a space group descriptive of the structure of a crystal, which has been conventionally obtained by assembling a plastic model or by calculation on the desk, at a high speed and with efficiency.

Further, even when a space group descriptive of a crystal structure having a high symmetricalness is determined, there is no room for occurrence of human errors, and hence a space group can be determined with a high reliability.

The foregoing is considered as illustrative only of the principle of the present invention. Further, since numerous modifications and changes will readily occur to those skilled in the art, it is not desired to limit the invention to the exact construction and applications shown and described, and accordingly, all suitable modifications and equivalents may be regarded as falling within the scope of the invention in the appended claims and their equivalents.

What is claimed is:

1. A method of determining a space group descriptive of a structure of a target crystal defined by input data, said method comprising the steps of:

determining a crystal system to which the structure of the target crystal belongs, said structure being stored on a first disk;

performing packing processing by use of a plurality of space groups included in said crystal system and stored on a second disk;

performing comparison between each of a plurality of crystal structures obtained by said packing processing and said structure of said target crystal, and determining, when data of one of said plurality of crystal structures obtained from a corresponding one of said plurality of space groups by said packing processing agrees with data of said structure of said target crystal, that said corresponding one of said plurality of said space groups is one descriptive of said structure of said target crystal; and displaying results of the performing step on a display.

2. The method of determining a space group descriptive of a structure of a crystal as claimed in claim 1, wherein said packing processing is performed by performing arithmetic operation on atom coordinates of each atom constituting said structure of said target crystal by use of matrices corresponding to each of said plurality of space groups included in said crystal system, and determining equivalent positions of said each atom by said arithmetic operation.

3. The method of determining a space group descriptive of a structure of a crystal as claimed in claim 1, wherein said comparison between said each of a plurality of crystal structures obtained by said packing processing and said structure of said target crystal is performed at least by comparing a number of atoms, and a name of each atom.

* * * * *

UNITED STATES PATENT AND TRADEMARK OFFICE
CERTIFICATE OF CORRECTION

PATENT NO. : 5,590,053
DATED : December 31, 1996
INVENTOR(S) : Tatsuya ITO et al.

It is certified that error appears in the above-indentified patent and that said Letters Patent is hereby corrected as shown below:

Col. 2, line 66, change "the figure" to --Fig. 1--.
Col. 3, line 49, change "the figure" to --Fig. 2--.
Col. 4, line 26, change "the figure" to --Fig. 5--.
Col. 5, line 24, delete "this figure" and insert --FIGS. 9(A), 9(B), and 9(C)--; and
line 35, delete "in respect of" and insert --with respect to--.
Col. 6, line 66, change "affix" to --affixed--.
Col. 8, line 20, delete "this"; and
line 21, change "figure" to --Fig. 16--.

Signed and Sealed this

Twenty-seventh Day of May, 1997

Attest:

BRUCE LEHMAN

*Attesting Officer*     *Commissioner of Patents and Trademarks*